US00PP24641P2

(12) United States Plant Patent
Pan

(10) Patent No.: US PP24,641 P2
(45) Date of Patent: Jul. 15, 2014

(54) ***LANTANA* PLANT NAMED 'LANZ0004'**

(50) Latin Name: ***Lantana camara* L.**
Varietal Denomination: LANZ0004

(75) Inventor: Shifeng Pan, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 153 days.

(21) Appl. No.: 13/507,782

(22) Filed: Jul. 27, 2012

(51) Int. Cl.
*A01H 5/00* (2006.01)

(52) U.S. Cl.
USPC ..... Plt./227

(58) Field of Classification Search
USPC ..... Plt./227
See application file for complete search history.

*Primary Examiner* — Wendy C Haas
(74) *Attorney, Agent, or Firm* — Joshua L. Price

(57) ABSTRACT

A new *Lantana* plant named 'LANZ0004' particularly distinguished by the large sized white flowers with a yellow throat, excellent floriferousness because of limited seed set, and dense mounding habit with medium green foliage.

1 Drawing Sheet

Latin name of the genus and species of the plant claimed: *Lantana camara* L.

Varietal denomination: 'LANZ0004'.

BACKGROUND OF THE NEW PLANT

The present invention comprises a new *Lantana*, botanically known as *Lantana camara* L., and hereinafter referred to by the variety name 'LANZ0004'.

'LANZ0004' is a product of a planned breeding program. The new cultivar 'LANZ0004' has large sized white flowers with a yellow throat, excellent floriferousness because of limited seed set, and dense mounding habit with medium green foliage.

'LANZ0004' originates from a self-ed hybridization in a greenhouse in July 2007 in Gilroy, Calif. USA. The female parent was an unpatented, proprietary plant identified as '168-3' with pink flower color, a shorter plant habit, and fewer branches when compared to 'LANZ0004'. The seed was sown in November 2007 in Gilroy, Calif.

'LANZ0004' was selected as one flowering plant within the progeny of the stated cross in May 2008 in a greenhouse in Gilroy, Calif.

The first act of asexual reproduction of 'LANZ0004' was accomplished when vegetative cuttings were propagated from the initial selection in the May 2008 in a greenhouse in Gilroy, Calif.

BRIEF SUMMARY OF INVENTION

Horticultural examination of plants grown from cuttings of the plant initiated in May 2008 in Gilroy, Calif., and continuing thereafter, has demonstrated that the combination of characteristics as herein disclosed for 'LANZ0004' are firmly fixed and are retained through successive generations of asexual reproduction.

'LANZ0004' has not been observed under all possible environmental conditions. The phenotype may vary significantly with variations in environment such as temperature, light intensity, and day length.

A Plant Breeder's Right for this cultivar was applied for in Canada on Nov. 28, 2011, No. 11-7428. 'LANZ0004' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0004' with colors being as true as possible with an illustration of this type.

Figure 1:
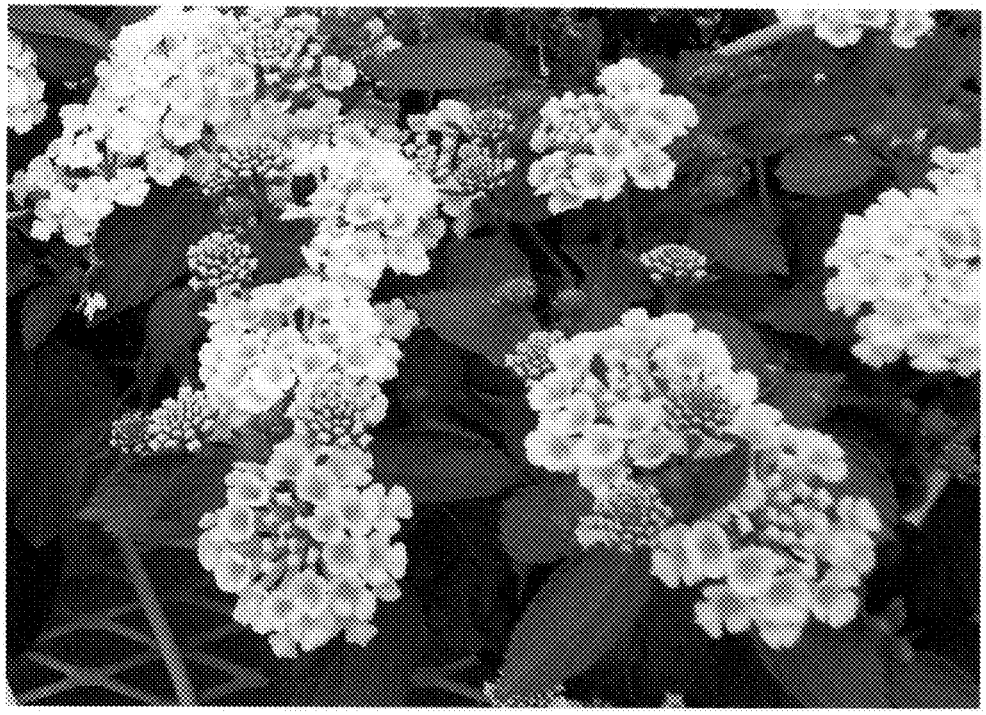
Figure 2:
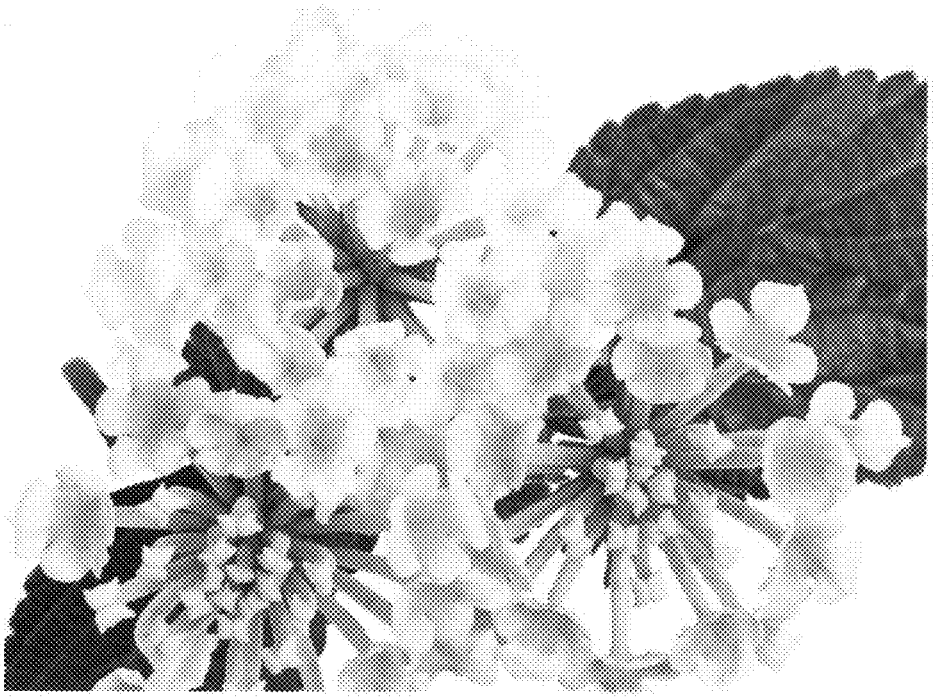

The photographic drawings show in FIG. 1 four flowering plants of the new variety and in FIG. 2 a close-up of the inflorescences.

DETAILED BOTANICAL DESCRIPTION

The plant descriptions and measurements were taken in Gilroy, Calif. under natural light in May 2012. These plants were approximately 16 weeks old and were growing in 1 gallon pots in a greenhouse trial. The plants used for the photographs were about 15 weeks old growing in a greenhouse trial and the photographs were taken in September 2011.

Color chart used: Royal Horticultural Society Colour Chart (R.H.S.) 2001.

TABLE 1

DIFFERENCES BETWEEN THE NEW VARIETY 'LANZ0004' AND A MOST SIMILAR VARIETY

| | 'LANZ0004' | 'Ban Whit' (U.S. Plant Pat. No. 21,590) |
|---|---|---|
| Floret size: | Larger | Smaller |
| Bud color: | Brighter yellow | Duller yellow |
| Foliage sheen: | More glossy | Less glossy |
| Plant height: | Taller | Shorter |
| Flower timing: | 3-5 days earlier | Later |

Plant:

*Form, growth and habit*.—Semi-woody, grown as an annual or perennial; compact and dense mounding habit; well branched.

*Plant height*.—28-30.0 cm.

*Plant height* (*inflorescence included*).—27-30.0 cm.

*Plant width*.—35-39.0 cm.

Foliage:

*Type*.—Opposite.

*Immature, leaf color, upper surface*.—Closest to RHS 147A but a little less yellow.

*Lower surface*.—Closest to RHS 147B.

*Mature, leaf color, upper surface*.—Closest to RHS 147A but a little less yellow.

*Lower surface*.—Closest to RHS 147B.

*Length*.—5.4-5.6 cm.

*Width*.—3.4-3.7 cm.

*Shape*.—Ovate.

*Base shape*.—Attenuate.

*Apex shape*.—Acute.

*Margin*.—Dentate.

*Texture, upper*.—Hirsute.

*Lower surface*.—Hirsute.

*Lower surface*.—RHS 144B.

*Pattern of veining*.—Pinnate.

*Petioles color*.—RHS 144B.

*Petioles length*.—0.7-0.8 cm.

*Diameter of petiole*.—0.2 cm.

*Texture*.—Hirsute with some very short glandular hairs.

Stem:

*Color of stem*.—RHB 144B.

*Length of stem*.—20-24.0 cm.

*Diameter*.—0.25 cm.

*Length of internodes*.—0.5-2.0 cm.

*Texture*.—Pilose, hirsute.

Inflorescence:

*Type*.—Umbel like, flattened semi-sphere the florets are sessile on an ovate receptacle.

*Blooming habit*.—Flowers continuously from spring through fall.

*Number of open flowers per inflorescence*.—25-30.

*Quantity of inflorescences per plant*.—About 50 plus another 40 umbels with only buds forming.

*Lastingness of individual blooms on the plant*.—About 4 weeks (depending on temperatures).

*Fragrance*.—Slightly spicy.

*Umbel horizontal diameter*.—About 4.5 cm.

*Umbel vertical height*.—2.1-2.5 cm.

*Peduncle color*.—RHS 144A.

*Length of peduncle*.—About 3.0 cm.

*Peduncle diameter*.—0.15 cm.

*Texture*.—Hirsute, glandular hairs.

Corolla:

*Floret form*.—Salver-shaped to shallow cup-shaped, with a relatively long tube at the base. Each flower subtended by a single bract.

*Immature, color of petals, upper surface*.—RHS 4C quickly becoming closer to RHS N155C with a throat of RHS 9A.

*Lower surface*.—RHS 4D.

*Length of floret*.—0.9-1.0 cm.

*Width of floret*.—1.0-1.1 cm.

*Depth of floret*.—1.8-2.0 cm.

*Mature, color petals, upper surface*.—RHS N155C with a throat of RHS 9A to RHS 9D; maturing to all white.

*Lower surface*.—Closest to RHS N155D.

*Petal length*.—0.3-0.4 cm.

*Petal diameter*.—0.3-0.4 cm. Apex: Slightly mucronulate. Margin: Entire. Shape: Obovate. Degree of lobation: Moderate. Texture, upper surface: Papillose. Lower surface: Papillose.

*Corolla tube, color, outer surface*.—Closest to RHS N155D.

*Color, inner surface*.—Closest to RHS N155D.

*Corolla tube length*.—0.5 cm.

*Diameter* (*at opening*).—0.1 cm.

*Corolla tube texture, outer surface*.—Pubescent.

*Inner surface*.—Hirsute.

Bud (just before opening):

*Color*.—RHS 6D.

*Length*.—1.2-1.5 cm.

*Width*.—0.3-0.4 cm at the apex.

*Shape*.—Tubular with a flared apex.

Bract:

*Color*.—Closest to RHS 144B with a RHS 144A apex.

*Length*.—0.5-0.6 cm.

*Diameter*.—0.2 cm.

*Texture, upper surface*.—Hirsute.

*Lower surface*.—Hirsute.

Calyx:

*Number of sepals*.—5, fused sepals forming a short tube around the base of each floret.

*Color of sepals*.—RHS 147D.

*Length of sepals*.—0.35 cm.

*Width of sepals*.—0.2 cm.

*Apex shape*.—Obtuse.

*Apex margins*.—Entire.

*Texture, outer surface*.—Pubescent.

*Inner surface*.—Glabrous.

Reproductive organs:

*Gynoecium*.—

*Pistil quantity*.—1.

*Length*.—0.4 cm.

*Style color*.—RHS 155C.

*Style length*.—0.2 cm.

*Stigma color*.—RHS 1C.

*Ovary color*.—RHS 145C with a RHS 145A apex.

*Ovary length*.—0.15 cm.

*Ovary diameter*.—0.1 cm.

*Androecium*.—

*Stamen quantity*.—4.

*Color of filaments*.—RHS 1C.

*Length filaments*.—0.6-0.7 cm.

*Anther color*.—RHS 3A.

*Length of anthers*.—0.1 cm.

*Color of pollen*.—RHS 11B.

*Pollen amount*.—Normal.

Fertility/seed set: Has not been determined to date.

Disease/pest resistance: Has not been determined to date.

What is claimed is:

1. A new and distinct variety of *Lantana* plant named 'LANZ0004' substantially as illustrated and described herein.

* * * * *